United States Patent
Gorobets et al.

(10) Patent No.: US 11,638,769 B1
(45) Date of Patent: May 2, 2023

(54) DEVICE FOR DISINFECTANT AGENT APPLICATION AND GENERATION AND METHOD OF USE

(71) Applicant: PLASMIUS, INC, Redmond, WA (US)

(72) Inventors: Vladimir Leonidovich Gorobets, Redmond, WA (US); Andrey Makarov, Moscow (RU); George Goldman, Tel Aviv (IL); Nadezhda Gulko, Moscow (RU)

(73) Assignee: PLASMIUS, INC, Redmond, WA (US)

( * ) Notice: Subject to any disclaimer, the term of this patent is extended or adjusted under 35 U.S.C. 154(b) by 0 days.

(21) Appl. No.: 17/990,238

(22) Filed: Nov. 18, 2022

Related U.S. Application Data

(60) Provisional application No. 63/281,389, filed on Nov. 19, 2021.

(51) Int. Cl.
*A61L 2/22* (2006.01)
*A61L 2/24* (2006.01)
*B01J 19/08* (2006.01)
*A61L 101/02* (2006.01)

(52) U.S. Cl.
CPC ............... *A61L 2/22* (2013.01); *A61L 2/24* (2013.01); *B01J 19/088* (2013.01); *A61L 2101/02* (2020.08); *A61L 2202/11* (2013.01); *A61L 2202/14* (2013.01); *B01J 2219/0801* (2013.01);
(Continued)

(58) Field of Classification Search
CPC .......... A61L 2/22; A61L 2/24; A61L 2101/02; A61L 2202/11; A61L 2202/14; B01J 19/088; B01J 2219/0801; B01J 2219/0805; B01J 2219/0869; B01J 2219/0896
See application file for complete search history.

(56) References Cited

U.S. PATENT DOCUMENTS 7,008,592 B2   3/2006   Sias et al.
2021/0069360 A1   3/2021   Shane et al.

FOREIGN PATENT DOCUMENTS

DE   202020005219   4/2021
RU   2670654   10/2018
(Continued)

OTHER PUBLICATIONS

English-language machine translation of RU2670654 (Year: 2018).*
English-language machine translation of RU201413 (Year: 2020).*

*Primary Examiner* — Timothy C Cleveland
(74) *Attorney, Agent, or Firm* — Leonid Kisselev

(57) ABSTRACT

A device for obtaining and applying a disinfectant agent and method of use are provided. The device includes a pre-processing cascade unit that activates (ionizes) air, with the activated air being supplied by an air pump to an inlet of a sprayer, where the activated air mixes with an initial working fluid (distilled water) to form an activated air-working fluid aerosol mixture that is sprayed by the sprayer into a reactor of cone-shaped volumetric cold plasma that includes divergent discharge electrodes. The device further includes a unit for generating high-voltage pulses of a nanosecond duration that is connected to the discharge electrodes and that causes the electrodes to generate electrical discharges. Upon the mixture coming into contact with the electrical discharges, potent disinfectant agents (such as peroxynitrite and one or more peroxynitrite's precursors or derivatives) are synthesized and expelled from the device.

20 Claims, 9 Drawing Sheets

(52) U.S. Cl.
CPC ............... *B01J 2219/0805* (2013.01); *B01J 2219/0869* (2013.01); *B01J 2219/0896* (2013.01)

(56) References Cited

FOREIGN PATENT DOCUMENTS

| | | | | |
|---|---|---|---|---|
| RU | 201413 | 12/2020 | | |
| WO | WO-2011149188 A2 | * 12/2011 | ............... | A61L 2/14 |

* cited by examiner

40

DEVICE FOR DISINFECTANT AGENT APPLICATION AND GENERATION AND METHOD OF USE

FIELD

This application relates in general to disinfectology and sanitation, and in particular, to a device for disinfectant agent generation and application and method of use.

BACKGROUND

In the age of the COVID-19 pandemic and abundance of other infectious agents, disinfection of spaces occupied by people, including homes, business spaces, and private and public transportation vehicles, as well as of food and drink used for human consumption, is of primary importance. While traditional disinfectants, such as chlorine-based solutions, can be used for disinfection in many circumstances, they require extensive labor to apply over a significant surface area, leave an unpleasant smell, and are often unsuitable for application to food and drink used for human consumption. Accordingly, attempts have been made to develop automated disinfection devices, but the results are inadequate for a variety of reasons.

For example, U.S. Pat. No. 7,008,592, issued Mar. 7, 2006, to Sias et al., the disclosure of which is incorporated by reference, discloses a device for obtaining disinfectant liquid that includes a vessel for the cleaning fluid, a fluid pump, a fluid sprayer, a pulsed high-voltage power supply, and two discharge plates. The cleaning fluid mist is activated, creating cleaning fluid mist, by passing the fluid between the two electrode plates. Disinfection is achieved by exposing surfaces to be treated to the activated cleaning fluid mist. One disadvantage of this device is the low efficiency of processing the jet of the cleaning fluid with the electric discharge because the discharge area is smaller than the diameter of the jet of the cleaning fluid, and not all of the fluid is activated. Another disadvantage is the lack of air in the discharge area because the mass of the sprayed fluid in the discharge area is much greater than the mass of the air.

Another a device for obtaining a disinfectant agent is disclosed in Russian Federation Patent No. RU2670654, published Oct. 24, 2018. The disclosed device includes a vessel for working liquid, a liquid pump, an air pump, a liquid sprayer, a pulsed high-voltage power supply, a discharge control unit and a system of three or four electrodes. Disinfection is achieved by exposing the surfaces to be treated to droplets of activated liquid (active mist). The activated liquid is created by exposing the working liquid to a rotating plasma discharge generated by three or four electrodes. The disadvantages of the device are the insufficient efficiency of processing the jet of the working liquid with the electric discharge due to the design features of the liquid sprayer and the electrode system used, as a result of which not all of the working liquid is activated. In addition, in such a device, there is a risk of "dry" combustion of plasma (in the absence of a water-air mixture at the outlet of the liquid sprayer) because there is no synchronization of the operating modes of the air and liquid pumps with the discharge control unit. Further, for the activated liquid to act as a disinfectant agent, the working liquid must have a hydrogen peroxide in a concentration of 3-5%, which makes the disinfectant agent unsuitable for many circumstances where the treated surfaces can come in contact with a human, such as if the treated surfaces are on food to be ingested by a human.

A still further device is disclosed by Russian Federation Patent No. RU201413U1, granted Dec. 14, 2020, entitled "Device for obtaining a disinfectant." The disadvantages of the device is the lack of protection against "dry" combustion of the plasma arc, as well as the need to use a weak solution of hydrogen peroxide, in concentration from 0.2% to 1%, to increase the activity of the disinfectant agent.

A still further device is disclosed by German Patent No. DE202020005219 U1, entitled "Portable device for the production of bactericidal, virocidal and fungicidal aerosols by ionization of the sprayed solution, gel or powder substance with cold plasma for disinfection of materials, objects and surfaces," to Gulko et al., published Apr. 8, 2021. The disadvantages of this device is the requirement for a presence in the initial working solution of hydrogen peroxide in a concentration of 0.2 to 1%, as well as high power consumption necessary to achieve the required degree of disinfection.

A still further device is described in U.S. Patent Application Publication No. US20210069360, entitled "Decontamination Device and Method Using Nonthermal Plasma Actuator," published Mar. 11, 2021, to Shane et al., the disclosure of which is incorporated by reference. A cleaning fluid reservoir is provided in which a cleaning fluid includes a source of an active species for disinfecting an object or an enclosed space. The source of the active species is hydrogen peroxide and the active species is hydroxyl ions. The cleaning fluid does not contain silver, chlorine, or peracetic acid. The cleaning fluid reservoir is cavitated by applying force to the cleaning fluid. A mist is generated at substantially one atmosphere ambient pressure, comprising aerosol droplets accumulating in a top chamber portion of a substantially closed chamber comprising a funnel shaped top chamber portion, a bottom chamber portion, a side chamber portion and an interior chamber portion, wherein the mist is generated from the cleaning fluid while the cleaning fluid is subject to cavitation by force; the mist is subjected to a nonthermal plasma actuator to form plasma activated ionic particles carried by the aerosol droplets of the mist, wherein the plasma activated ionic particles are hydroxyl ions, and wherein the nonthermal plasma actuator is a DC arc. The use of this device includes the use of hydrogen peroxide as a source of the active substance in the initial cleaning fluid, which significantly limits the scope of the device for disinfection of objects, products and surfaces that impose increased requirements on the level of environmental friendliness and safety of the agents used by the disinfectant, and also increases the cost of disinfection due to the need to use special cleaning fluid: a concentrated solution of hydrogen peroxide. Further, use of as an active substance of short-lived hydroxyl ions significantly reduces the effectiveness of the resulting disinfectant agent.

Accordingly, there is a need for a device that can generate and apply a highly effective disinfectant agent in an environmentally friendly, safe, and efficient manner.

SUMMARY

The device and method described below provide an improved way of obtaining a disinfectant agent that addresses the shortcomings of known analogues, as well as provides an expansion of the arsenal of techniques and devices used for this purpose. The technical result achieved by the device and method is producing an environmentally friendly, highly active disinfectant agent, while increasing the efficiency, safety and efficiency of the device as compared to known analogues. The technical result is achieved due to the structure and operation of the device. In addition to including a power supply, a tank for an initial working fluid, a liquid pump, and an air pump, the device also includes a pre-processing cascade unit that activates (ionizes) air, with the activated air being supplied by the air pump to an inlet of a sprayer included in the device, where the activated air mixes with the initial working fluid (provided to the inlet by the liquid pump) to form an activated air-working fluid aerosol mixture that is sprayed by the sprayer into a reactor that includes divergent discharge electrodes that generate discharges of cone-shaped volumetric cold plasma that widen towards the ends of the electrodes. The device further includes a unit for generating high-voltage pulses of a nanosecond duration that is connected to the discharge electrodes and that causes the electrodes to generate the electrical (plasma) discharges of a nanosecond duration under a control of a control module included in the device. Upon the mixture of the working fluid and the activated air coming into contact with the electrical discharges, potent disinfectant agents (such as at least one of peroxynitrite and peroxynitrite's precursors or derivatives) are synthesized and expelled from the device. As the initial working fluid is pure distilled water (without any impurities or additives such as including hydrogen peroxide), the resulting disinfecting agents are environmentally safe and can be applied to a wide variety of surfaces, including that of food, water, and spaces occupied by humans, including offices spaces, living spaces, and vehicles. The surfaces to which the disinfecting agents can be applied can also include plants (including cannabis plants), allowing to reduce amount of pathogenic organisms present on the plants without the use of pesticides that could be harmful if consumed by humans).

In one embodiment, a device for disinfectant agent generation and application is provided. The device includes a power supply module configured to provide current pulses; a tank in which an initial working solution is stored; a liquid pump that pumps the initial working fluid to an inlet of a sprayer; a first plasma reactor that ionizes air using cold plasma upon provision of the current pulses into the first plasma reactor by the power supply module; an air pump that pumps the ionized air to the inlet of the sprayer; the sprayer that sprays an aerosol mixture of the ionized air and the initial working fluid into a second reactor; the second reactor including divergent discharge electrodes; a high-voltage pulse generation unit that applies high-voltage electrical pulses to the divergent discharge electrodes, wherein the divergent discharge electrodes form electrical discharges upon the application of the pulses and wherein disinfectant agents are synthesized upon the aerosol mixture encountering the electrical discharges; an outlet within the second reactor through which an aerosol including the disinfectant agents escape towards a surface to be disinfected; and a controller in control of the high-voltage pulse generation unit, the air pump, the liquid pump and the power supply module.

In a further embodiment, a method for disinfectant agent generation and application is provided. A method for disinfectant agent generation and application. The method includes: pumping by a liquid pump an initial working fluid from a tank to an inlet of a sprayer; ionizing air using cold plasma in a first plasma reactor via providing by a power supply current pulses into the first plasma reactor; pumping by an air pump the ionized air to an inlet of a sprayer; spraying by the sprayer an aerosol mixture of the ionized air and the initial working fluid into a second reactor including divergent discharge electrodes; applying using a high-voltage pulse generation unit high-voltage electrical pulses to the divergent discharge electrodes to form electrical discharges upon and synthesized disinfectant agents upon the aerosol mixture encountering the electrical discharges, wherein an aerosol including the disinfectant agents escapes towards a surface to be disinfected from an outlet of the second reactant; and controlling via a controller the high-voltage pulse generation unit, the air pump, the liquid pump and the power supply module.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

The device described below implements a fundamentally improved layout, being in the form of a portable wireless monoblock with an autonomous power supply, providing an increase in efficiency, potency of disinfectant agent production, as well as the safety of the device while reducing the weight and energy characteristics of the device.

Figure 1:
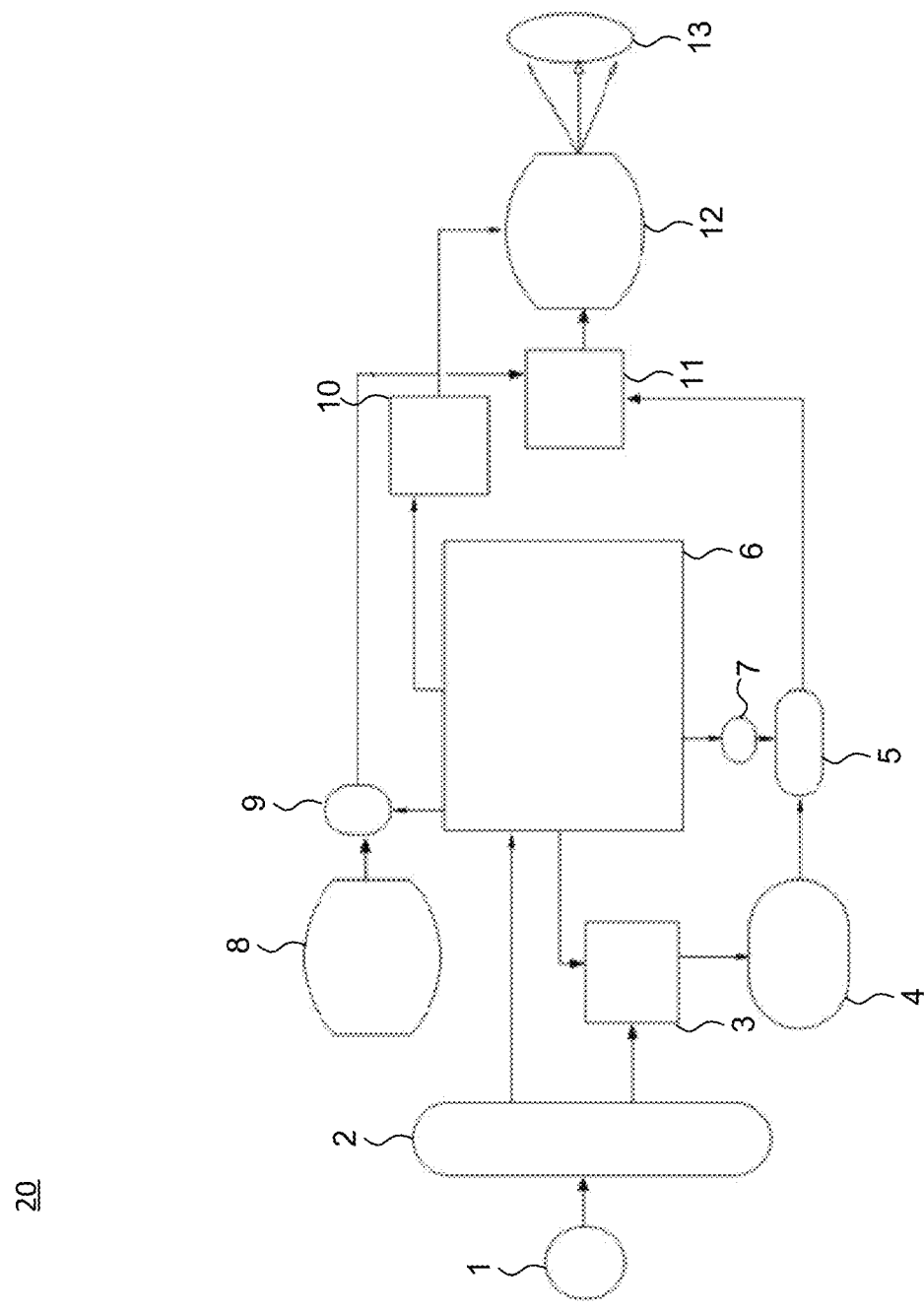
FIG. 1 is a block diagram of a device for obtaining and applying a disinfectant agent in accordance with one embodiment.
Figure 7:
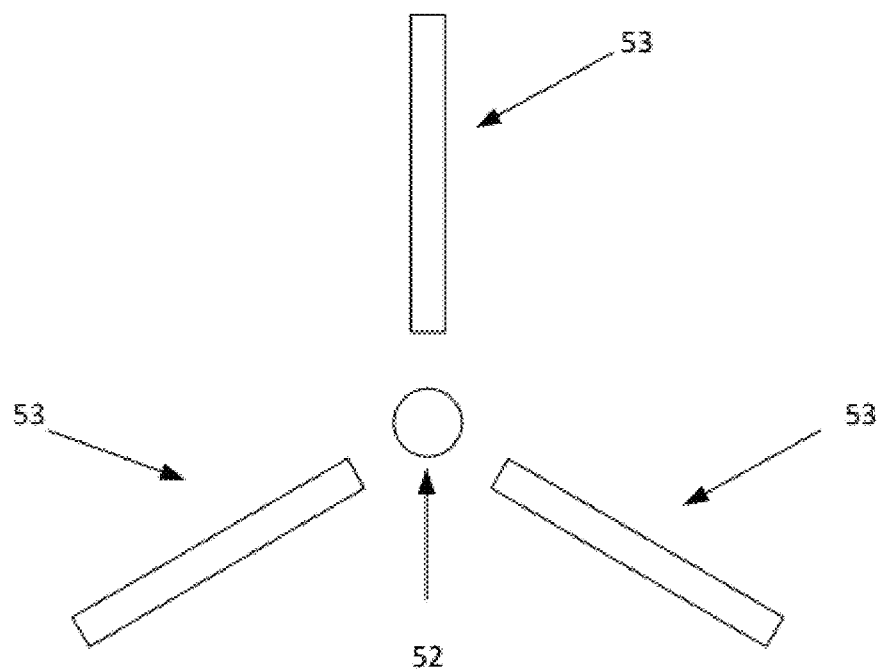
FIG. 7 is a diagrams showing three discharge electrodes of a second reactor accordance with one embodiment.
Figure 8:
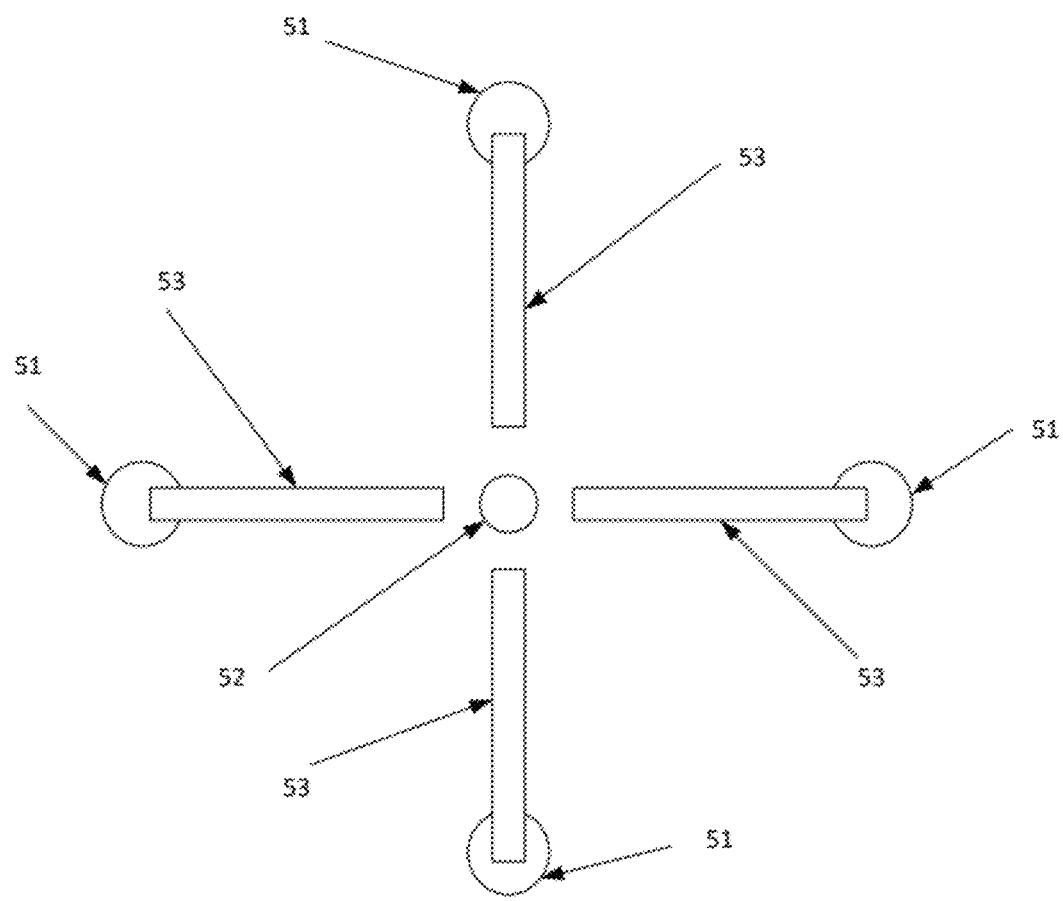
FIG. 8 is a diagram showing four of the discharge electrodes of a second reactor in accordance with one embodiment.
Figure 9:
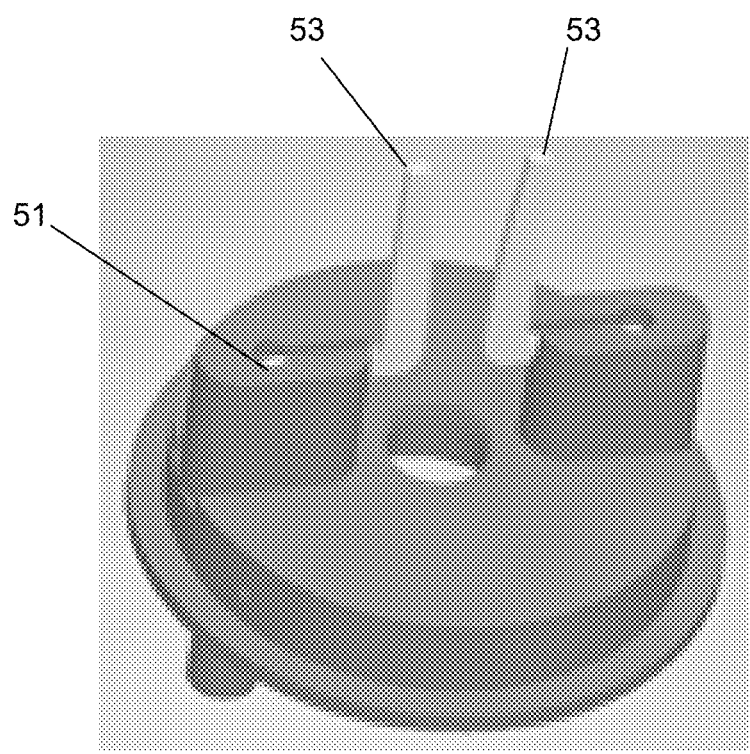
FIG. 9 is a diagram showing the two discharge electrodes for use in a second reactor embedded in an insulated holder in accordance with one embodiment.

FIG. 1 is a block diagram of a device 20 for obtaining and applying a disinfectant agent in accordance with one embodiment. In one embodiment, the device 20 is a portable wireless monoblock with an autonomous power supply 1 (such as a battery, which can be a rechargeable battery). The output of the autonomous power supply 1 is connected to the input of the voltage converter 2 that controls the electronics and power units of the device 20. The first output of the voltage converter 2 is connected to the control board of a microcontroller control unit 6 (which includes a microcontroller and is also referred to as a control module 6 below), and the second output of the voltage converter 2 is connected with a voltage converter 3 for the air compressor 4 (also referred to as air pump 4). An output of the microcontroller control unit 6 is connected via a power supply module 7 that generates pulses applied to an electrode within the primary activation reactor 5 (also referred to as a pre-activation cascade unit 5 and primary plasma reactor 5 below), which is described in more detail below with reference to FIG. 5. Another output of the microcontroller control unit 6 is also connected to a liquid pump 9 that supplies distilled water from the built-in tank 8 to a sprayer 11 (also referred to as a spray nozzle 11). Another output of the microcontroller control unit 6 is connected to the module 10 that forms high-voltage pulses 10 that are applied to discharge electrodes that are within a second plasma reactor 12 (also referred to as a reactor of cone-shaped volumetric cold plasma 12 and cone-shaped volumetric cold plasma 12 below). The output of the primary plasma reactor 5 is connected by an airline to the sprayer 11. The sprayer 11 outputs an aerosol mixture of water and air activated by the primary plasma reactor 5 (where the water is mixed with the activated air and is activated (ionized), for the first time, by the activated air)to the second plasma reactor 12. At the outlet of the second plasma reactor 12, a disinfection aerosol 13 is formed that acts as a disinfecting agent and can be applied to surfaces of interest. The electrodes within the second plasma reactor 12 can be knife-shaped with beveled and rounded edges, though in a further embodiment, other shapes of the electrodes are possible (such as sinusoidal shape, rectangular shape, or blade-shaped, though still other shapes are possible). The material of the discharge electrodes within the second plasma reactor can be tungsten or stainless steel, though in a further embodiment, other materials are possible. If the second plasma reactor 12 includes three discharge electrodes 12, they can be distributed relative to each other at 120°. The discharge electrodes are located in the second plasma reactor 12 in such a way that the discharge arising between them is perpendicular to the plane of the passing flow of the sprayed liquid, thereby ensuring the passage of the sprayed liquid through the plasma formed by the electrodes. The number of the discharge electrodes is at least two, but can include three, four, or more than four electrodes. An example of such positioning is seen with reference to FIGS. 7, 8, and 9. FIG. 7 is a diagram showing three discharge electrodes 53 of a second reactor 12 accordance with one embodiment. Cone-shaped plasma 52 is formed between the electrodes. The electrodes are held in place using holders 51 made of insulating material. FIG. 8 is a diagram showing four of the discharge electrodes 53 of a second reactor 12 in accordance with one embodiment. Similarly, each of the electrodes 53 are held in place using a holder 51 made of an insulating material. The cone-shaped plasma discharges 52 are formed between the electrodes 53. The advantages of using three or four discharge electrodes are disclosed in the Russian Federation Patent No. RU2670654, cited above, but as describe above, other numbers of electrodes are also possible. For example, the plasma discharges 51 could be formed between two electrodes shown with reference to FIG. 9. FIG. 9 is a diagram showing the two discharge electrodes 53 for use in a second reactor 12 embedded in an insulated holder 51 in accordance with one embodiment. Still other electrode shapes are possible.

Returning to FIG. 1, the tank 8 with the initial solution is connected to the input of the liquid pump 9. During operation of the device 20, the spray nozzle 11 is fed an initial working solution (distilled water) from the tank 8 by the liquid pump 9. At the same time, air is activated (ionized) by the pre-activation cascade unit 5 and is supplied under pressure (such as substantially 1.5-2.2 bars, though other pressures are possible) to the spray nozzle 11 by the air pump 4 (which initially provides under pressure the air into the first plasma reactor 5, with the pressure continuing to push the (now ionized) air towards the spray nozzle even after the air exits from the pre-activation cascade unit 5), resulting in aerosol mixture of water and activated air being sprayed out of the spray nozzle 11. The sprayed aerosol mixture passes through a cone-shaped bulk discharge region formed by two or more diverging discharge electrodes in the second plasma reactor 12, with the water that is part of the aerosol mixture being activated a second time. Active particles (disinfectant agents) are formed in a cone-shaped volumetric discharge region, and due to the momentum imparted to the air-water mixture by the sprayer 11, continue to move towards the surface to be treated (at which the device 20 is directed) upon exiting the second plasma reactor 12, with the whole aerosol mixture 13 acting as the disinfectant agent due to the presence of the active particles.

The use of the pre-processing cascade unit 5 in combination with the second plasma reactor in the device 20 allows for double ionization of distilled water as a starting material to obtain a disinfectant with high disinfectant properties as the output. Subsequent to processing of the distilled water at by the pre-processing cascade unit, reactions in the second plasma reactor trigger the production of active substances that in their disinfectant activity exceed several times disinfectants such as chlorine dioxide and other oxygen-containing disinfectants. In particular, in reactor of cone-shaped volumetric cold plasma, active particles synthesized from the doubly-activated water include at least one of peroxynitrite and one or more of precursors or derivatives of peroxynitrite. In one embodiment, the concentration of the peroxynitrite in the liquid portion of the aerosol can be $(2\pm1)\times10^{-5}$ moles/liter, though other concentrations are also possible. The concentration is sufficient to destroy a wide range of pathogens with disinfection efficiency of at least 99.999% under certain conditions. However, peroxinitrite as well as peroxinitrite decompose quickly following the formation into substances safe for human consumption (such as water, nitrogen, and oxygen), edible susbtances on which the device 20 is used can be consumed by humans within a short time of application of the aerosol.

The control module 6 synchronizes the operating modes of the air pump 4, the primary ionization reactor 5 and the liquid pump 9 with a high-voltage pulse generation unit 10. The control module 6 monitors the operating pressure at the inlet of the sprayer nozzle 11 (such as through a pressure sensor positioned at the inlet and interfaced to the control module 6) that is due to the flow water-air aerosol mixture, based on the pressure, generates control signals for the operations of the high-voltage pulse generation unit 10. In particular, if no sufficient pressure at the inlet of the sprayer nozzle 11 is present, the high-voltage pulse generation unit is not by the control module 6 commanded to generate any electrical pulses. The control module 6 provides the formation of such a cyclic feedback algorithm for controlling the operation of the device 20, including when the device is turned on and off, which prevents the possibility of "dry ignition" (maintenance) of the electric discharge in the reactor of the cone-shaped volumetric cold plasma 12 when there is no working pressure of the air flow at the inlet of the sprayer nozzle 11 of the water-air mixture. In a further embodiment, in addition to controlling the formation of the cold plasma, based on the existing pressure at the nozzle inlet, the control module 6 can up or down regulates the work done by the air pump 4 to lower or increase the pressure.

To optimize the spatio-temporal characteristics of the processing of the initial working solution in the second plasma reactor, a cone-shaped volumetric electric discharge is formed due to a special design of the system of three or more divergent discharge electrodes within the second plasma reactor 12, to which a high-frequency voltage with an amplitude of up to 30 kV is supplied through the high-voltage pulse generation unit 10. The term "volumetric" in relation to the electric discharge refers to the cone-like shape of the electric discharge in three-dimensional space. The frequency of the applied pulses can be in the range of 1 kHz to 150 kHz. The pulses applied to the electrodes can be of a rectangular shape. In a further embodiment, the current applied to the discharge electrodes can be sinusoidal instead of pulse-shaped. In one embodiment, the power of the electric discharge is from 100 W to 200 W, though in a further embodiment, other values are also possible. At the same time, the flow of air-liquid mixture through the sprayer 11 at this discharge power (100 W to 200 W) should be 20-30 ml/min, preferably 30-60 ml/min. Operating voltages and currents are set by the high-voltage pulse generation unit 10 in such a way that the electric discharges (cold plasma) that occur between the electrodes in the second plasma reactor 12 is of a nanosecond duration.

In one embodiment, the first output of the control module 6 is connected to the input of the liquid pump, the second output of the control module to the input of the air pump, the third output of the control module to the unit for generating high-voltage pulses of a nanosecond duration of the cone-shaped volumetric cold plasma reactor, the fourth output of the control module connected to the double DBD reactor of the pre-processing cascade unit. The control module can control the parts to which the control module is connected in this way.

The device 20 can further include a user-interfacing component (not shown) that allow the user to turn the device on and off, and, optionally, control the parameters of the device's 20 operations, such as how long the device is to stay on or the amount of the disinfectant agent produced. Such user interfacing components can be one or more tactile buttons, a touch screen display on which different options can be displayed, though still other user-interfacing components are possible. In a further embodiment, the device 10 can include a wireless transceiver interfaced to the microcontroller control unit 6 via which the device 20 can receive wireless commands from a user, such as a via a mobile app operating on the user's mobile device.

In one embodiment, the optimal distance between the discharge electrodes of the device 20 and the treated surface is the distance not closer than 1 meter and not further than 2 meters, though in a further other optimal distances are possible. To make sure that the device 20 is within the optimal distance range, the device 20 can further include a laser controller (not shown) that can be positioned at the same level (relative to the surface being treated) as the discharge electrodes. The laser controller 14 includes a laser distance sensor and determines a current distance between the electrodes and the surface in front of the electrodes, and if the distance is outside of the optimal distance range, the laser controller 14 provides an alert to a user, which can be a light or a sound signal, or a message sent to a user's mobile device if the light controller 14 is interfaced to a wireless transceiver (such as a wireless transceiver interfaced to the microcontroller control unit 6). The laser controller 14 can include an independent power supply and an independent microcontroller, or be operated by the microcontroller control unit 6 of the device and powered by the autonomous power supply 1. Even if the controller 14 has a built-in power supply and microcontroller, the laser controller 14 can be interfaced to the microcontroller control unit 6 and start operation at the same time as the rest of the device 20 based on a command from the microcontroller control unit 6; alternatively, or in addition, the laser controller 14 can include an independent switch that initiates the operations of the laser controller 14. In a further embodiment, other ways to determine the distance between the electrodes and the surface are possible.

In a still further embodiment, instead or in addition to having an autonomous supply, the device 20 can be connectable to a source of AC power, such as an electric power grid via a wall socket, and be able to use the AC power either to recharge the autonomous power supply or use the AC power directly.

Figure 2:
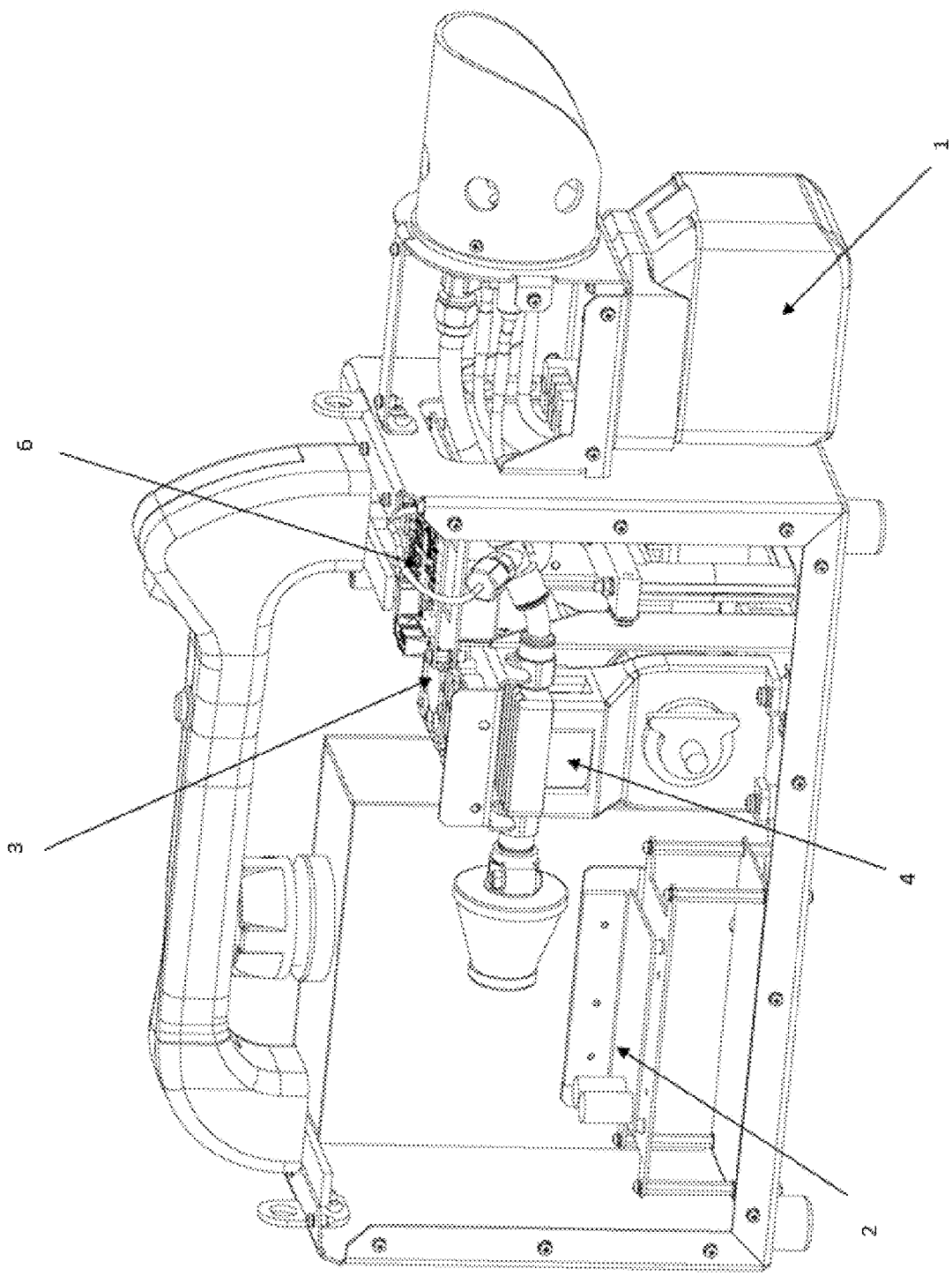
FIGS. 2-4 provide several views of an external appearance of the device of FIG. 1 in accordance to one embodiment.
Figure 3:
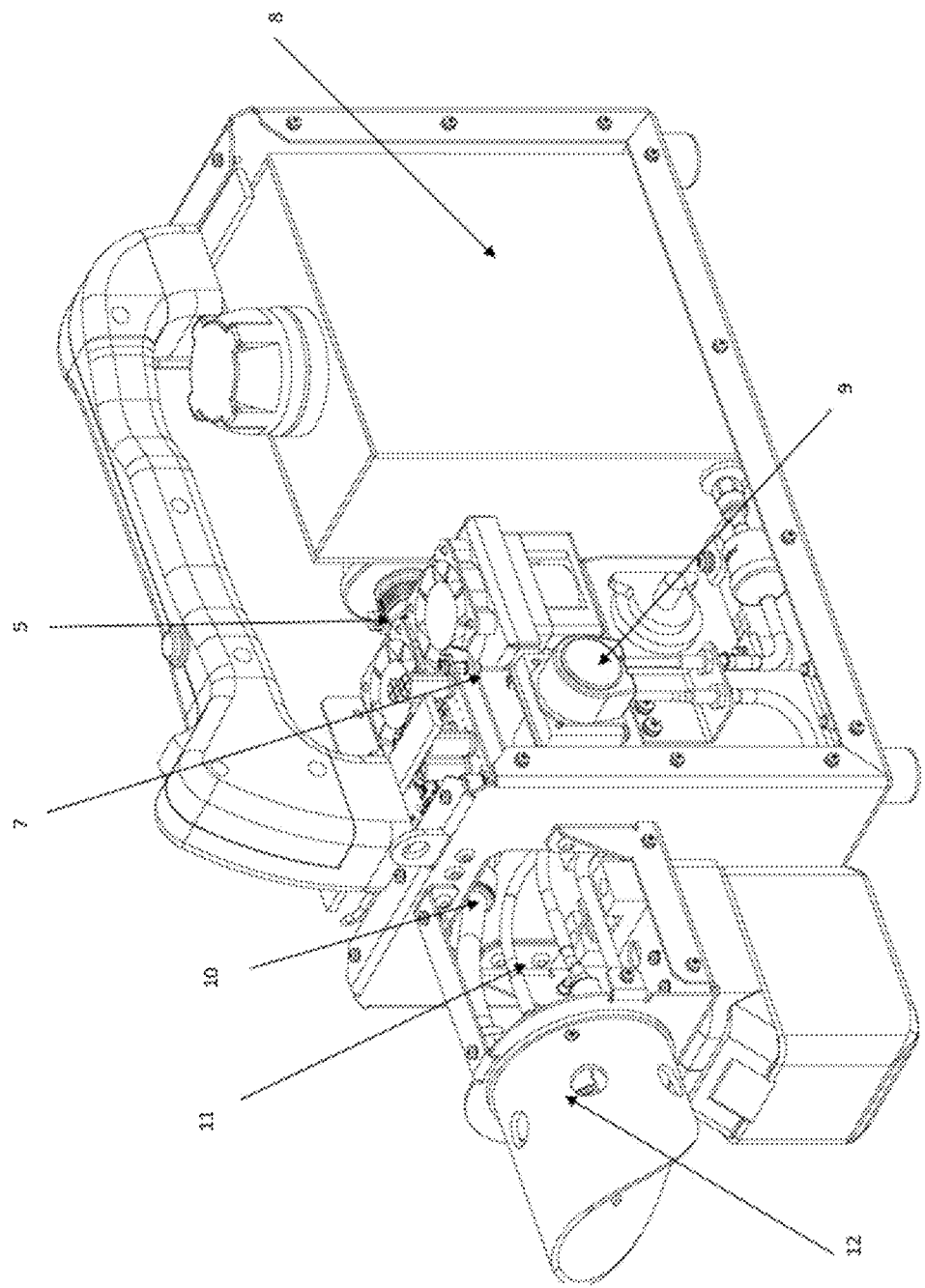
Figure 4:
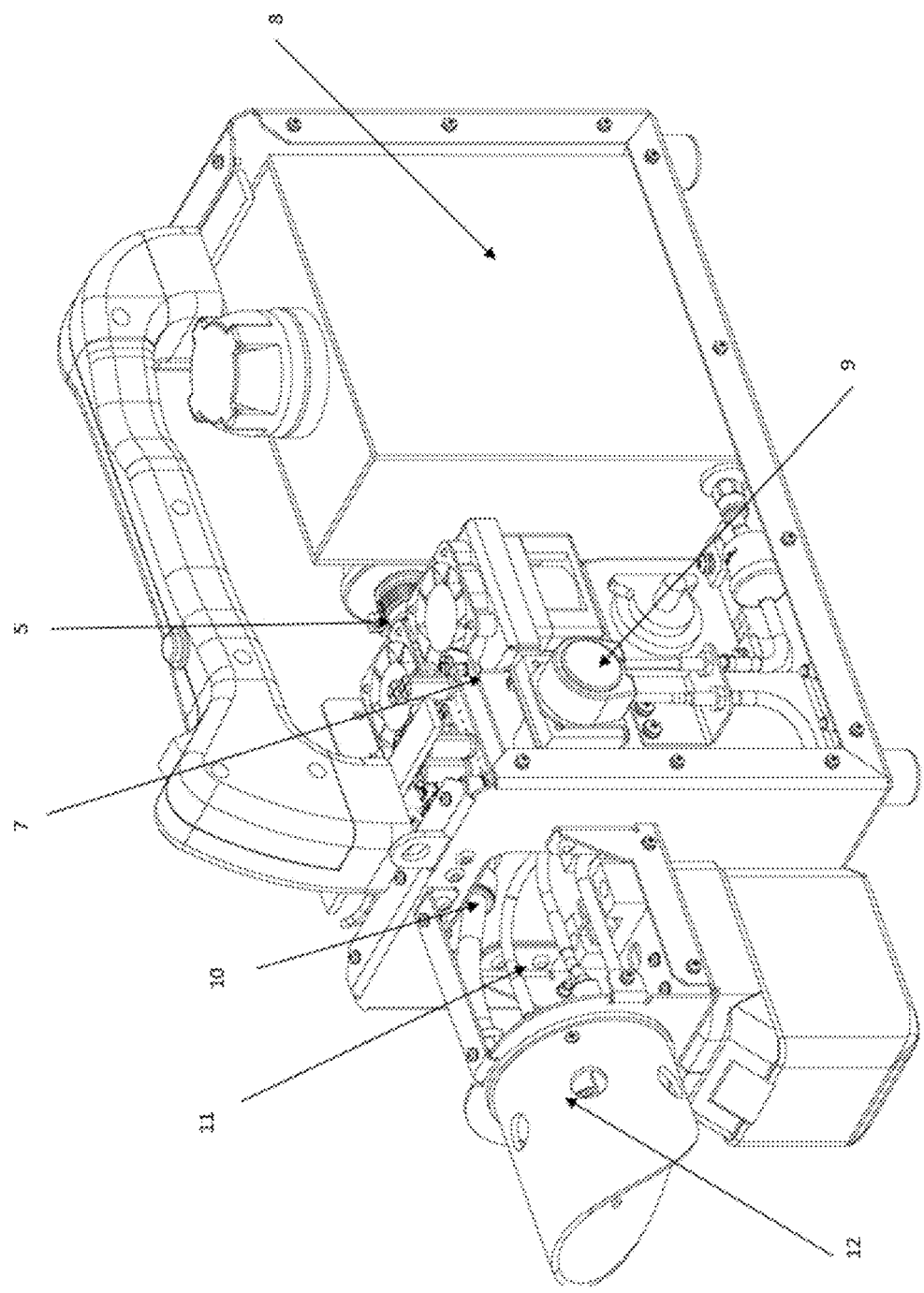

While the physical appearance of the device 20 can take many forms, FIGS. 2-4 provide several views of an external appearance of the device 20 of FIG. 1 in accordance with one embodiment. Other shapes of the device 20 are possible.

Figure 5:
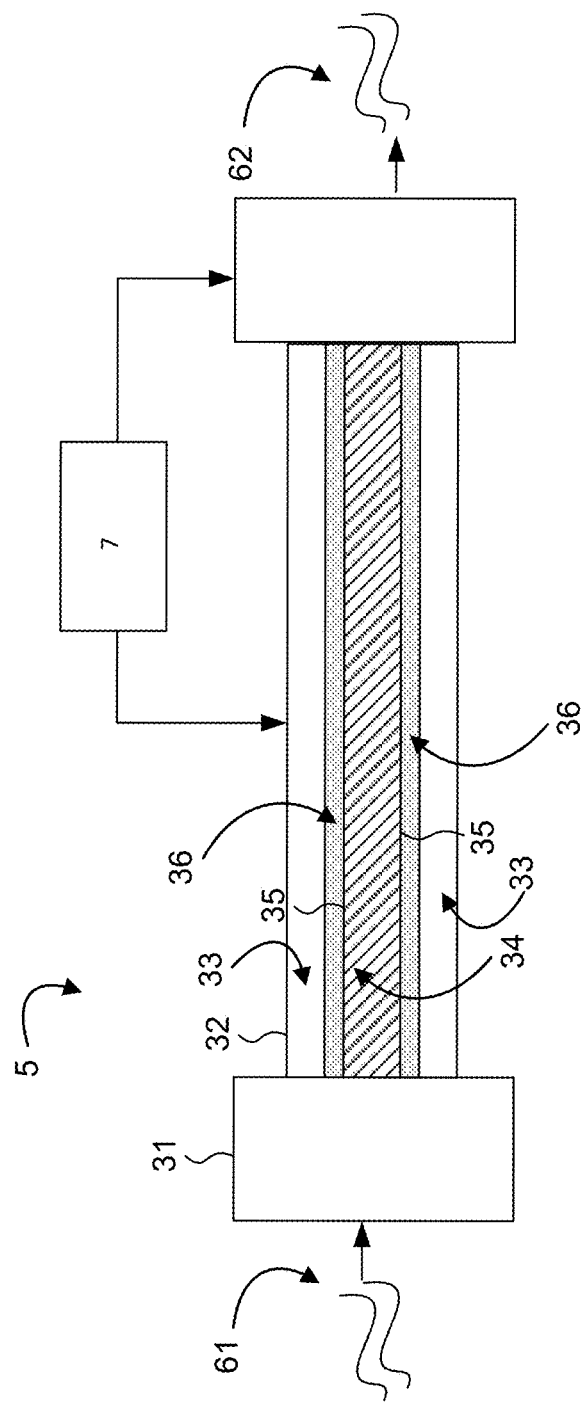
FIG. 5 is a diagram showing a design the pre-processing cascade unit of the device of FIG. 1 implemented as a DBD reactor in accordance with one embodiment.

The use of the pre-processing cascade unit 5 provides ionized air that, in the mixture with the distilled water, allows for the formation of the peroxynitrous compounds that act as disinfectant agents upon existing the device 20. The pre-processing cascade unit 5 can be a doubledielectric-barrier-discharge (DBD) reactor that outputs activated, ionized air in the required concentration, which enters the input of the second plasma reactor 12. FIG. 5 is a diagram showing a design the pre-processing cascade unit of the device 20 of FIG. 1 implemented as a DBD reactor in accordance with one embodiment. The pre-processing cascade unit 5 includes a metal vessel 32 that includes an air inlet nozzle 31 through which air 61 from the air compressor 4 enters the metal vessel 32, with the nozzle 31 made of an insulating material (such as fluoroplastic, though other materials are possible). The pre-processing cascade unit 5 further includes a pipe 33 made out of an insulating material with a diameter of 8-10 mm (though a different diameter is possible if dimensions of the unit change), a central metal electrode 34 coated with porous ceramics 35, and a passage 36 for activated air 62 through which the activated air leaves the reactor 5, still being moved by the pressure provided by the air pump 5 to move towards the spray nozzle 11. The central metal electrode 34 is housed within the insulating pipe 33, with the passage 36 formed between the electrode 34 and the pipe 33 allowing the activated air to travel out of the unit 5. In one embodiment, the insulating pipe 33 can be made out of quartz glass. In a further embodiment, alternatively, or in addition to quartz, the insulating pipe 33 can be made out of aluminum oxide ($Al_2O_3$). While quartz glass is easier to shape into a desired configuration than aluminum oxide, quartz glass is transparent and allows to see discharges within the unit 5, both quartz glass and aluminum oxide can be used for the pipe 33 as they are both resistant to ozone and ultraviolet radiation that forms within inside the pre-processing cascade unit 5 unlike a lot of other insulating materials such as plastics. However, in a further embodiment, still other insulating materials that are resistant to ozone and ultraviolet radiation can be used.

Double dielectric barrier discharges (cold plasma) form between the central metal electrode 34 and the metal vessel 32 (which acts as a ground electrode) upon application of the high-voltage pulses of nano-second duration to the electrode 34, with the insulating pipe 33 acting as one insulating barrier for the discharges and the porous ceramics 35 acting as a secondary insulating barrier. The power supply module 7 is a generator of high-voltage pulses of nanosecond duration that applies the high-voltage pulses of a nanosecond duration to the electrode 34, which in turn causes the generation of the double dielectric barrier discharges (cold plasma) within the pipe 33 that causes the ionization of the air 61. The generator can generate alternating sinusoidal, impulse, rectangular, and continuous current. The cold plasma generated by the electrode 34 can be based on a corona discharge, either a positive corona discharge or a negative corona discharge, though other kinds of cold plasma are also possible. The use of high-voltage pulses of nanosecond duration allows to avoid streamer discharges and to obtain a homogeneous non-equilibrium plasma that activates the air. The voltage and frequency of the pulses are selected in such a way to allows to obtain the necessary degree of air ionization with ratios $O^-$ and $O_3$ that are optimal for subsequent plasma-chemical transformations in the second plasma reactor 12 of the device 20.

In one embodiment, the voltage can be in the range of substantially 7 kV-12 kV, with the frequency being in the 15 kHz-100 kHz range, though in a further embodiment other values of voltage and frequency are possible.

In one embodiment, the electrode 34 is cylindrical (though other shapes are also possible) and the entire surface of the cylinder that faces the pipe 33 is covered with the porous ceramics 35. The presence of the porous ceramics 35 on the electrode 34 allows for double, as opposed to single, dielectric barrier discharges to be formed inside the pipe 33, with the double dielectric barrier discharges having a higher efficacy due to requiring less energy for their creation and creating more cold plasma than single dielectric barrier discharges. Further, the presence of the pores (openings) in the ceramics 35 allows to homogenize the cold plasma being created due to each of the discharges originating in one of the pores. As the pores are spread out homogeneously throughout the surface of the electrode 34 that faces the pipe 33, cold plasma forms homogenously between the pipe 33 and the electrode 34, thus allowing to homogeneously activate the air 61 passing through the passage 36 between the electrode 34 and the pipe 33. In one embodiment, the size of the pores can be 50 micrometers-80 micrometers, though in a further embodiment, other sizes are possible.

Figure 6:
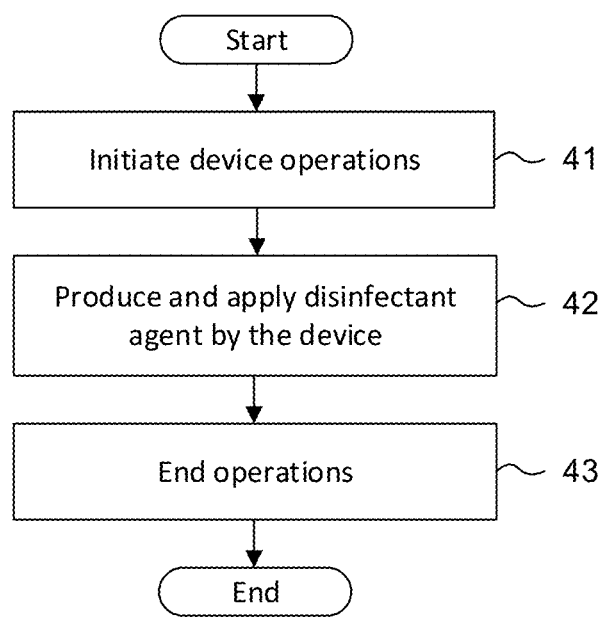
FIG. 6 is flow diagram showing a method of operation of the device in accordance with one embodiment.

Using the device 20 allows to apply the disinfectant agent to any desired accessible surface, including one that will come into contact or will be consumed by a human, such as food or drink. Further, the disinfectant agent produced by the device 20 can be applied to plants, including cannabis plants, allowing to reduce presence of pathogenic organisms on the plants without the use of pesticides that could be harmful to humans if either ingested or consumed in other ways, such as through smoke produced by the plant being lit on fire (such as in case of cannabis). FIG. 6 is flow diagram showing the method 40 of operation of the device 20 in accordance with one embodiment. The operations of the device 20 are initiated (step 41), which can be done manually via the user interfacing components on the device or wirelessly via a wireless transceiver included in the device 20, and if any parameters for operation were entered, the device continues to function in accordance with those parameters. Generation and expulsion of the disinfectant agent is performed by the device 20, as described in detail above (step 42). Briefly, the spray nozzle 11 is fed an initial working solution (distilled water) from the tank 8 by the liquid pump 9. At the same time, air is activated by the pre-activation cascade unit 5 and is supplied under pressure (such as 1.5 bar to 2.2 bar, though other values are also possible) to the spray nozzle 11 by the air pump 4, resulting in aerosol mixture of water and activated air being sprayed out of the spray nozzle 11. The sprayed aerosol mixture passes through a cone-shaped bulk discharge region formed by three or more diverging discharge electrodes in the volumetric cold plasma reactor 12. Active particles are formed in a cone-shaped volumetric discharge region, and due to the momentum imparted to the air-water mixture by the sprayer 11, continue to move towards the surface to be treated upon exiting the second plasma reactor 12. The operation of the device is stopped (step 43), ending the method. The stop of operation can be caused either by receiving a direct command from a user (such as a press of a button or a wireless command), or due to predetermined conditions, such as preset operating time running out.

While the invention has been particularly shown and described as referenced to the embodiments thereof, those skilled in the art will understand that the foregoing and other changes in form and detail may be made therein without departing from the spirit and scope of the invention.

The invention claimed is:

1. A device for disinfectant agent generation and application, comprising:
    a power supply module configured to provide current pulses;
    a tank in which an initial working solution is stored;
    a liquid pump that pumps the initial working fluid to an inlet of a sprayer;
    a first plasma reactor that ionizes air using cold plasma upon provision of the current pulses into the first plasma reactor by the power supply module;
    an air pump that pumps the ionized air to the inlet of the sprayer;
    the sprayer that sprays an aerosol mixture of the ionized air and the initial working fluid into a second reactor;
    the second reactor comprising divergent discharge electrodes;
    a high-voltage pulse generation unit that applies high-voltage electrical pulses to the divergent discharge electrodes, wherein the divergent discharge electrodes form electrical discharges, each of the electrical discharges comprising further cold plasma, upon the application of the pulses and wherein disinfectant agents are synthesized upon the aerosol mixture encountering the electrical discharges;
    an outlet within the second reactor through which an aerosol comprising the disinfectant agents escapes towards a surface to be disinfected; and
    a controller in control of the high-voltage pulse generation unit, the air pump, the liquid pump and the power supply module.

2. A device for disinfectant agent generation and application according to claim 1, wherein the initial working fluid consists of only distilled water.

3. A device for disinfectant agent generation and application according to claim 1, the first plasma reactor further comprising:
    a metal vessel comprising an air inlet nozzle into which the air is pumped by the air pump;
    an insulating pipe within the metal vessel;
    a metal electrode covered with porous ceramics and positioned within the insulating pipe, wherein the current pulses are high-voltage current pulses of nano-second duration and an application of the high-voltage current pulses of nano-second duration by the power supply module to the electrode causes formation of double dielectric barrier discharges between the metal vessel and the metal electrode that comprise the cold plasma that ionizes the air; and a passage formed between the insulating pipe and the metal electrode through which the ionized air exits the first plasma reactor.

4. A device for disinfectant agent generation and application according to claim 3, wherein the high-voltage current pulses of nano-second duration are one or more alternating sinusoidal, impulse, rectangular, and continuous pulses.

5. A device for disinfectant agent generation and application according to claim 3, wherein the insulating pipe comprises one of quartz and aluminum oxide.

6. A device for disinfectant agent generation and application according to claim 1, wherein the electrical discharges formed by the divergent discharge electrodes are perpendicular to a plane of movement of the aerosol mixture through the second reactor.

7. A device for disinfectant agent generation and application according to claim 1, wherein the further cold plasmas formed by the divergent discharge electrodes form cone-shaped volumetric cold plasma.

8. A device for disinfectant agent generation and application according to claim 1, the high-voltage electrical pulses applied to the divergent electrodes are at least one of rectangular-shaped and sinusoidal.

9. A device for disinfectant agent generation and application according to claim 1, wherein the disinfectant agents comprise at least one of peroxynitrite and one or more of precursors or derivatives of peroxynitrite.

10. A device for disinfectant agent generation and application according to claim 1, further comprising:
a pressure sensor positioned at the inlet of the sprayer and configured to sense a pressure at which the aerosol mixture exits the sprayer; and
the controller interfaced to the pressure sensor and configured to control the application of the high-voltage electrical pulses to the divergent discharge electrodes based on the sensed pressure.

11. A device for disinfectant agent generation and application according to claim 10, further comprising:
the controller further configured to at least one of up regulate and down regulate work done by the air pump based on the sensed pressure.

12. A device for disinfectant agent generation and application according to claim 1, further comprising:
a laser controller comprising a laser distance sensor configured to measure a distance a portion of the second reactor and the surface to be disinfected, wherein the laser controller provides an alert based on the distance.

13. A device for disinfectant agent generation and application according to claim 12, the laser controller further comprising a microcontroller different from the controller.

14. A device for disinfectant agent generation and application according to claim 12, wherein the laser distance sensor is interfaced to the controller.

15. A device for disinfectant agent generation and application according to claim 1, further comprising a user interface through which the user commands for the controller are received.

16. A device for disinfectant agent generation and application according to claim 15, wherein the user interface comprises a wireless transceiver interfaced to the controller and the user commands are received wirelessly via the wireless transceiver.

17. A device for disinfectant agent generation and application according to claim 1, a power supply configured to supply power to the power supply module, the air pump, and the liquid pump.

18. A method for disinfectant agent generation and application, comprising steps of:
pumping by a liquid pump an initial working fluid from a tank to an inlet of a sprayer;
ionizing air using cold plasma in a first plasma reactor via providing by a power supply module current pulses into the first plasma reactor;
pumping by an air pump the ionized air to an inlet of a sprayer;
spraying by the sprayer an aerosol mixture of the ionized air and the initial working fluid into a second reactor comprising divergent discharge electrodes;
applying using a high-voltage pulse generation unit high-voltage electrical pulses to the divergent discharge electrodes to form electrical discharges, each of the electrical discharges comprising further cold plasma, and synthesizing disinfectant agents upon the aerosol mixture encountering the electrical discharges, wherein an aerosol comprising the disinfectant agents escapes towards a surface to be disinfected from an outlet of the second reactant; and
controlling via a controller the high-voltage pulse generation unit, the air pump, the liquid pump and the power supply module.

19. A method according to claim 18, wherein the current pulses are high-voltage current pulses of nano-second duration.

20. A device for disinfectant agent generation and application according to claim 18, wherein the initial working fluid consists of only distilled water.

* * * * *